(12) United States Patent
Stern et al.

(10) Patent No.: US 11,045,397 B2
(45) Date of Patent: Jun. 29, 2021

(54) HYGIENE PRODUCT POD AND METHODS OF USING SAME

(71) Applicant: Nohbo, LLC, Reston, VA (US)

(72) Inventors: Benjamin Gabriel Stern, Reston, VA (US); James J. Ramirez, Palm Bay, FL (US)

(73) Assignee: NOHBO, LLC, Palm Bay, FL (US)

( * ) Notice: Subject to any disclaimer, the term of this patent is extended or adjusted under 35 U.S.C. 154(b) by 0 days.

(21) Appl. No.: 16/675,990

(22) Filed: Nov. 6, 2019

(65) Prior Publication Data

US 2021/0128415 A1     May 6, 2021

(51) Int. Cl.
| | | |
|---|---|---|
| *A61K 8/02* | (2006.01) | |
| *A61Q 5/02* | (2006.01) | |
| *A61K 8/37* | (2006.01) | |
| *A61K 8/41* | (2006.01) | |
| *A61K 8/42* | (2006.01) | |
| *A61K 8/34* | (2006.01) | |
| *A61Q 5/12* | (2006.01) | |

(Continued)

(52) U.S. Cl.
CPC .............. *A61K 8/0204* (2013.01); *A61K 8/24* (2013.01); *A61K 8/345* (2013.01); *A61K 8/375* (2013.01); *A61K 8/41* (2013.01); *A61K 8/42* (2013.01); *A61K 8/8129* (2013.01); *A61Q 5/02* (2013.01); *A61Q 5/12* (2013.01); *A61K 2800/596* (2013.01); *A61K 2800/87* (2013.01)

(58) Field of Classification Search
CPC .. A61K 2800/87; A61K 8/0204; A61K 8/375; A61K 8/41; A61K 8/42; A61K 8/345; A61K 8/8129; A61K 8/24; A61K 2800/596; A61Q 5/02; A61Q 5/12
See application file for complete search history.

(56) References Cited

U.S. PATENT DOCUMENTS

| | | | |
|---|---|---|---|
| 3,081,267 A | 3/1963 | Laskey et al. | |
| 4,996,006 A | 2/1991 | Constantine et al. | |
| 5,062,994 A | 11/1991 | Imperatori | |

(Continued)

FOREIGN PATENT DOCUMENTS

| | | | |
|---|---|---|---|
| DE | WO2012055584 A2 | 5/2011 | |
| EP | 0896052 A1 | 10/1999 | |

(Continued)

OTHER PUBLICATIONS

Stepan, Personal Care Sulfate-Free, Jul. 2017 (Year: 2017).*

(Continued)

*Primary Examiner* — Trevor Love

(74) *Attorney, Agent, or Firm* — Greenberg Traurig, LLP (57) ABSTRACT

A hygiene product pod and a method of using the hygiene product pod, the hygiene product pod including a water soluble envelope and the hygiene product sealed in the envelope. The hygiene product includes surfactants in an amount ranging from about 10 wt % to about 40 wt %; polyols in an amount ranging from about 10 wt % to about 30 wt %; polyglyceryl fatty acid esters (PGEs) in an amount ranging from about 10 wt % to about 50 wt %; liquid amides in an amount ranging from about 5 wt % to about 40 wt %; and phospholipids in an amount ranging from about 0 wt % to about 20 wt %, wherein the hygiene product having a free water content of about 9 wt % or less.

21 Claims, 4 Drawing Sheets

(51) Int. Cl.
*A61K 8/81* (2006.01)
*A61K 8/24* (2006.01)

(56) References Cited

U.S. PATENT DOCUMENTS

| | | | |
|---|---|---|---|
| 5,756,438 A | 5/1998 | Rau et al. | |
| 5,824,629 A | 10/1998 | Petritsch | |
| 5,840,210 A | 11/1998 | Memula | |
| 5,951,991 A * | 9/1999 | Wagner | A61Q 19/10 424/401 |
| 5,990,058 A | 11/1999 | Bac et al. | |
| 6,566,313 B1 | 5/2003 | Hohenstein et al. | |
| 6,673,765 B1 | 1/2004 | Schulz et al. | |
| 6,753,451 B2 | 6/2004 | Nussbaum et al. | |
| 6,787,512 B1 | 9/2004 | Verrall et al. | |
| 7,115,254 B1 | 10/2006 | Brandt et al. | |
| 7,118,734 B1 | 10/2006 | Fuchshuber et al. | |
| 8,367,048 B2 | 2/2013 | Wells et al. | |
| 2002/0155962 A1* | 10/2002 | Cincotta | A61K 8/86 510/119 |
| 2002/0198119 A1 | 12/2002 | George | |
| 2007/0275064 A1 | 11/2007 | Mumoli | |
| 2008/0145426 A1* | 6/2008 | Amundson | A61K 8/733 424/484 |
| 2008/0152711 A1 | 6/2008 | Mumoli et al. | |
| 2009/0297569 A1 | 12/2009 | Hurwitz | |
| 2010/0313362 A1 | 12/2010 | Vainshelboim et al. | |
| 2010/0316586 A1* | 12/2010 | Knappe | A61K 8/8152 424/70.16 |
| 2011/0081392 A1 | 4/2011 | Arruda et al. | |
| 2012/0129955 A1* | 5/2012 | Bernhardt | C11D 3/3788 514/784 |
| 2013/0090279 A1 | 4/2013 | Hilvert et al. | |
| 2016/0067155 A1* | 3/2016 | Shimada | A61K 8/0212 424/44 |
| 2016/0143833 A1 | 5/2016 | Jeong | |
| 2016/0317397 A1* | 11/2016 | Wenz | A61K 8/44 |
| 2017/0259976 A1* | 9/2017 | Lee | C08K 9/10 |
| 2017/0298216 A1 | 10/2017 | LaBeque et al. | |
| 2018/0000733 A1 | 1/2018 | Chakrobotry | |
| 2018/0086523 A1* | 3/2018 | Ades | A61K 8/11 |
| 2018/0110699 A1* | 4/2018 | Conway | A61K 8/891 |
| 2018/0110709 A1* | 4/2018 | Smyth | A61K 8/463 |
| 2018/0311136 A1* | 11/2018 | Chang | A61K 8/463 |
| 2019/0216698 A1 | 7/2019 | Stern et al. | |

FOREIGN PATENT DOCUMENTS

| | | |
|---|---|---|
| JP | 2012144488 A | 8/2012 |
| JP | WO2014098268 A1 | 6/2014 |
| KR | 1020140111903 | 5/2015 |
| NL | 148102 | 12/1975 |
| WO | 93/07245 A2 | 4/1993 |
| WO | 01-01954 A1 | 1/2001 |
| WO | 02/22091 A1 | 3/2002 |
| WO | 2004082655 A1 | 9/2004 |
| WO | 2009153311 A2 | 12/2009 |
| WO | 2011/094690 A1 | 8/2011 |

OTHER PUBLICATIONS

Antiseptic Effect of a Topical Dermatological Formulation that Contains Hamamelis Distillate and Urea, M. Gloor et al., 2002 S. Karger GmbH, Freiburg (2 pages).
International Search Report and Written Opinion of the International Searching Authority for PCT/US2020/059166 dated Feb. 8, 2021.
International Search Report and Written Opinion of the International Searching Authority for PCT/US2019/014000 dated Apr. 29, 2019.
International Preliminary Report on Patentability for PCT/US2019/014000 dated Apr. 29, 2019.
International Search Report and Written Opinion of the International Searching Authority for PCT/US2016/042572 dated Oct. 21, 2016.
International Preliminary Report on Patentability for PCT/US2016/042572 dated Oct. 21, 2016.
Oatmeal in Dermatology: A Brief Review, Pazyar, et al., Indian Journal of Dermatology, Venerology and Leprology, Mar.-Apr. 2012, vol. 78, Issue 2.

* cited by examiner

HYGIENE PRODUCT POD AND METHODS OF USING SAME

FIELD

Aspects of the present disclosure provide a hygiene product pod configured for single-use applications, and a method of using such a pod.

BACKGROUND

Hygiene products, such as shampoo, bodywash, shaving cream, and conditioner are usually sold in a liquid or gel format. Such hygiene products generally contain active agents, such as surfactants and/or conditioners, in addition to significant amounts of water and/or viscosity control agents. Such hygiene products are most commonly provided in bottles containing enough product for many applications. While such products are suitable for many consumer applications, there is a need for smaller amounts of hygiene product, particularly in the travel and hospitality industries.

Hygiene products have been provided in small bottles for use in the hospitality and/or travel industries. However, the small bottles of shampoo/conditioner/shaving cream generally found in the hospitality industry have a high packaging to product ratio, which contributes to higher costs and excessive amounts of waste.

In addition, single-dose packages of shampoo/conditioner packaged in plastic sachets, bags, or blister packs have also been developed. However, such packaging is generally not recycled or biodegradable.

SUMMARY

Various embodiments include a hygiene product pod comprising a water-soluble envelope; and a hygiene product sealed in the envelope, the hygiene product comprising, based on the total weight of the hygiene product: surfactants in an amount ranging from about 10 wt % to about 40 wt %; polyols in an amount ranging from about 10 wt % to about 30 wt %; polyglyceryl fatty acid esters (PGEs) in an amount ranging from about 10 wt % to about 50 wt %; liquid amides in an amount ranging from about 5 wt % to about 40 wt %; and phospholipids in an amount ranging from about 0 wt % to about 20 wt %. The hygiene product having a free water content of about 9 wt % or less.

Various embodiments include a method of using a hygiene product pod comprising a water-soluble envelope and a hygiene product sealed in the envelope, the method including applying water to the pod to dissolve the envelope and release the hygiene product, applying the hygiene product to at least one body part of a user, and rinsing the hygiene product from the body part.

BRIEF DESCRIPTION OF THE DRAWINGS

The accompanying drawings, which are incorporated herein and constitute part of this specification, illustrate exemplary embodiments of the invention, and together with the general description given above and the detailed description given below, serve to explain the features of the invention.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

The word "exemplary" is used herein to mean "serving as an example, instance, or illustration." Any implementation described herein as "exemplary" is not necessarily to be construed as preferred or advantageous over other implementations.

It will also be understood that, as used herein, the terms "the," "a," or "an," mean "at least one," and should not be limited to "only one" unless explicitly indicated to the contrary. Thus, for example, reference to "a slot" includes examples having two or more slots unless the context clearly indicates otherwise.

Ranges can be expressed herein as from "about" one particular value, and/or to "about" another particular value. When such a range is expressed, examples include from the one particular value and/or to the other particular value. Similarly, when values are expressed as approximations, by use of the antecedent "about" or "substantially" it will be understood that the particular value forms another aspect. In some embodiments, a value of "about X" may include values of +/−1% X. It will be further understood that the endpoints of each of the ranges are significant both in relation to the other endpoint, and independently of the other endpoint.

Various embodiments relate to hygiene product pods in which the hygiene product is encapsulated in a water-soluble envelope in a single dose format. The hygiene product pods may provide cleansing and/or conditioning agents for hair and/or skin. In particular, the hygiene product includes active ingredients, such as active ingredients of a shampoo, conditioner, or a combination thereof, within a non-aqueous carrier that features polyols and polyglycerols.

The component weight percentages disclosed herein are based on the total weight of the hygiene product, unless otherwise specified.

Hygiene Product Pods

Various embodiments include single-dose hygiene products in the form of pods. Herein, the term "pod" refers to water-soluble envelope in the shape of a capsule, sphere, drop, or the like, filled with a hygiene product. For example, a pod may include an envelope encapsulating a liquid or gel of hygiene product. A pod may have any suitable shape and/or size. A pod may contain a sufficient amount of hygiene product for a single use. For example, a pod may contain an amount of shampoo sufficient to clean one head of hair, may contain an amount of bodywash sufficient to wash one body, or may contain an amount of a shaving product sufficient to shave one or more body parts. As used herein, the term "shaving product" may refer to shaving cream, shaving gel, or a precursor composition configured to form a shaving product.

In some embodiments, a pod containing shampoo, conditioner, or shampoo and conditioner may range in volume from about 4 g to about 12 g, such as from about 5 g to about 8 g. A pod containing bodywash may range in volume from about 6 g to about 15 g, such as from about 8 g to about 10 g. Pods including a concentrated active agent may be smaller than pods containing undiluted or semi-diluted active agents.

Figure 1A:
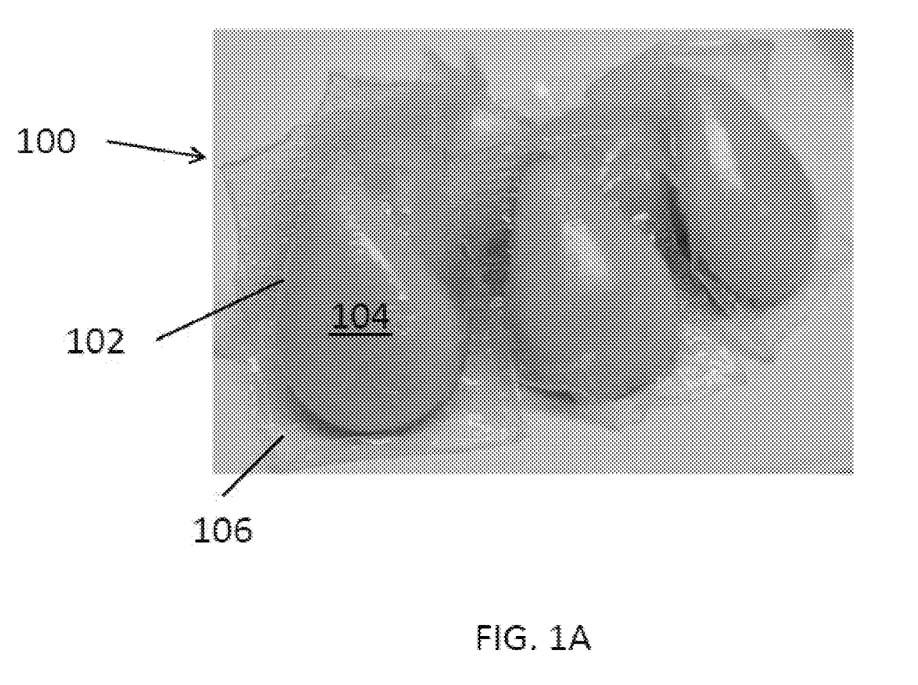
FIG. 1A photograph of the hygiene product pod various embodiments of the present disclosure.
Figure 1B:
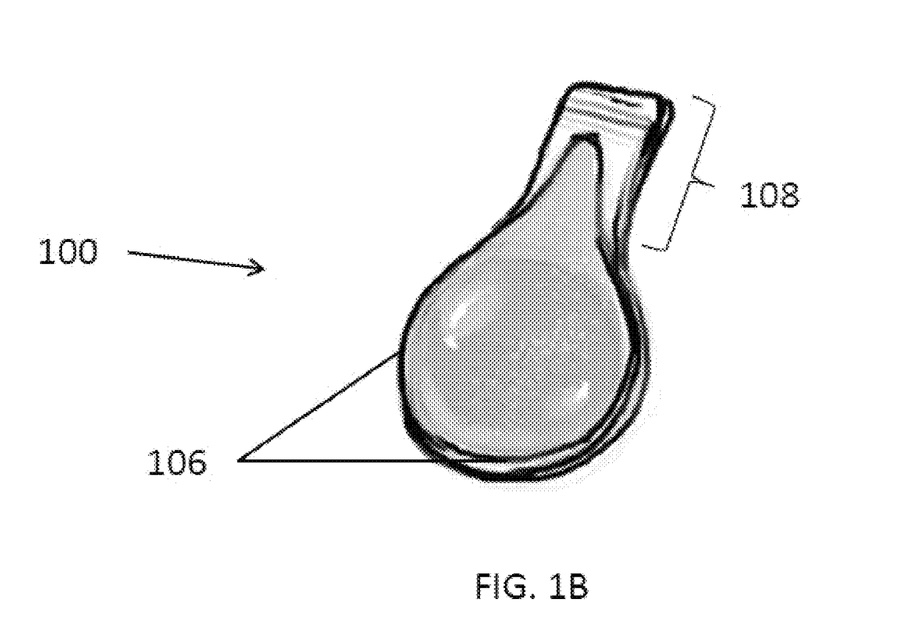
FIG. 1B is a perspective view of the pod of FIG. 1A after an optional cutting process.

FIG. 1A is a photograph of hygiene product pods 100, according to various embodiments. FIG. 1B is a perspective view of the pod 100 of FIG. 1A, after an optional trimming process. Referring to FIGS. 1A and 1B, the pod 100 includes a hygiene product 104 sealed in a water-soluble envelope 102. The pod 100 may be generally drop-shaped (as shown). However, the pod 100 is not limited to any particular shape. For example, the pod 100 may be rectangular, circular, triangular, square, pentagonal, circular, elliptical, tablet-shaped, or the like.

The envelope 102 may be configured to rapidly dissolve in the presence of a solvent such as water. For example, the envelope 102 may include or be formed of a water-soluble material, such as polyvinyl alcohol (PVOH), carboxymethyl cellulose (CMC), or the like. The water-soluble material may be in the form of a film or a woven or non-woven fiber, such as a PVOH or CMC fiber. For example, the envelope 102 may be formed of a PVOH film, such as Monosol 9643, available from Kuraray Inc.

The envelope 102 may have a thickness ranging from about 0.5 mm to about 5.0 mm. The envelope 102 may have a pH ranging from about 4.0 to about 9.0, at a temperature of about 25° C. The envelope 102 may be configured to dissolve in water at about 25° C. in a time period ranging from about 3 seconds to about 15 seconds, such as from about 5 seconds to about 7 seconds.

It has been found that forming the envelope 102 of PVOH may be particularly beneficial. For example, dissolved PVOH may act as a film-former (e.g., conditioning agent) and/or a foam-boosting agent. Accordingly, a PVOH envelope 102 may unexpectedly improve the properties of the hygiene product 104 by adding to suds, bubbles, and/or foam when in use.

The pod 100 may be formed by sealing two sheets or layers of the water-soluble material around the hygiene product 104. For example, the envelope 102 may be formed by placing the hygiene product 104 between two sheets of the water-soluble material, and then sealing the perimeters of the two sheets so as to form a seal region 106 that extends around the entire perimeter of the pod 100. In some embodiments, the sheets may be partially sealed (e.g., sealed along three sides) to form the envelope 102, after which the hygiene product 104 may be inserted into an open end of the envelope 102 followed by sealing of the open end to complete the pod 100.

In various embodiments, the sealing may be accomplished using any suitable sealing method. In some embodiments, the water-soluble material may be sealed using a heat sealing method. In other embodiments, the sealing may include the use of a water-soluble adhesive. In some embodiments, pods 100 may be formed using a packing machine, such as a Hydroforma packaging machine manufactured by Cloud Packaging Solutions, Des Plaines, Ill.

As shown in FIG. 1B, at least a portion of the seal region 106 may be optionally removed from the pod 100, to form a tab 108. For example, the envelope 102 may be cut during manufacturing of the pod 100. The tab 108 may operate as a contact point to facilitate handling of the pod 100 and/or removal of the pod 100 from product packaging.

In some embodiments, the pod 100 may optionally include an external moisture barrier. For example, the moisture barrier may be a hydrophobic coating or film applied to the outer surface of the envelope 102. In some embodiments, the moisture barrier may comprise hydrophobic esterified plant tri-glycerides, naturally occurring plant fats, or the like. In some embodiments, the moisture barrier may be configured to breakdown or dissolve in warm water.

Figure 2:
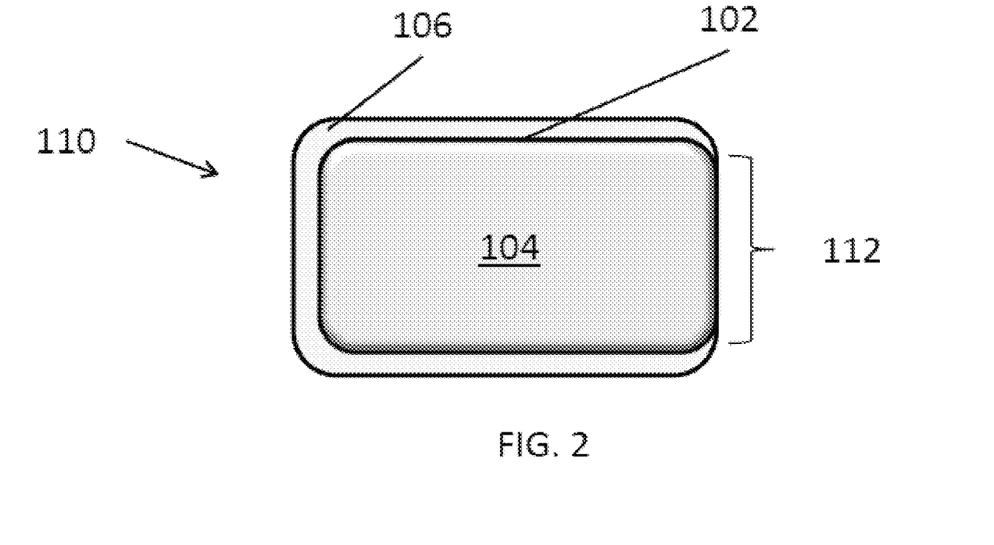
FIG. 2 is a top plan view of a hygiene product pod, according to various embodiments of the present disclosure.

FIG. 2 is a top plan view of a hygiene product pod 110, according to various embodiments. The pod 110 is similar to the pod 100, so only the differences therebetween will be described in detail.

Referring to FIG. 2, the pod 110 includes an envelope 102 in which a hygiene product 104 is disposed. In contrast to the pod 100 illustrated in FIG. 1, the envelope 102 is formed by sealing a single folded sheet of the water-soluble material around the hygiene product 104. As a result, the pod 110 includes a seal region 106 that extends along three sides of the hygiene product 104, and a folded region 112 that extends between opposing ends of the seal region 106.

Figure 3:
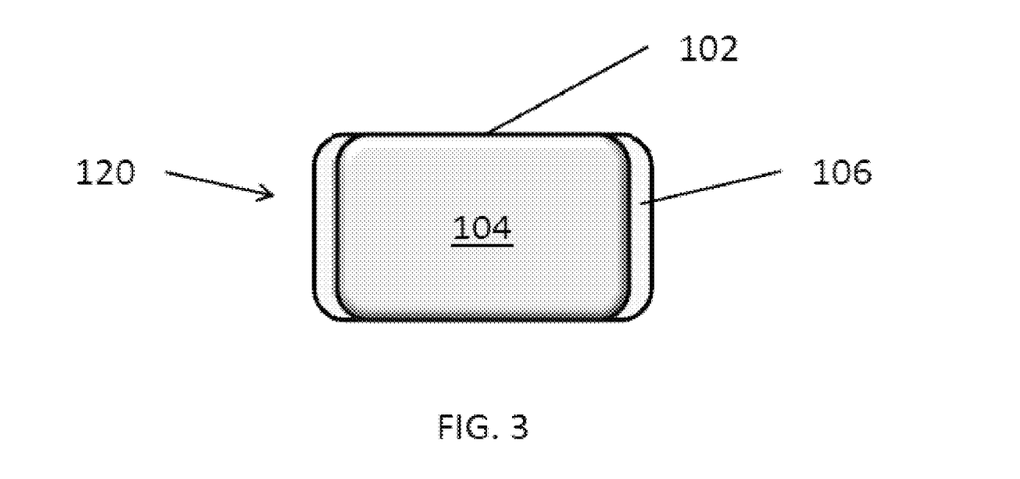
FIG. 3 is a top view of a hygiene product pod, according to various embodiments of the present disclosure.

FIG. 3 is a top view of a hygiene product pod 120 according to various embodiments. The pod 120 is similar to the pod 100, so only the differences therebetween will be described in detail.

Referring to FIG. 3, the pod 120 includes an envelope 102 in which a hygiene product 104 is disposed. In contrast to the pod 100 illustrated in FIG. 1, the envelope 102 is formed by sealing opposing ends of a tubular sheet of the water-soluble material in which the hygiene product 104 is disposed. As a result, the pod 120 includes seal regions 106 disposed at opposing ends of the pod 120.

While three methods of forming pods have been described above, the present disclosure is not limited to any particular method of envelope formation.

Hygiene Products

Conventional liquid hygiene products such, as conventional liquid shampoos, include substantial amount of water as a carrier. As a result, water-based shampoos cannot be stably encapsulated in a water-soluble envelope, since the high water content prematurely dissolves the envelope.

In contrast, non-aqueous solid hygiene products, such as dry shampoos, may be stably encapsulated in a water-soluble envelope. However, non-aqueous hygiene products do not provide the rheological properties and ease of use provided by conventional water-based shampoos and desired by consumers. As a result, non-aqueous hygiene products have experienced only limited commercial success.

According to various embodiments, the present hygiene product may be a substantially non-aqueous liquid or gel. For example, the hygiene product may have a free water content of about 9 wt % or less, such as about 5 wt % or less. For example, the hygiene product may have a free water content ranging from about 1 wt % to about 9 wt %, from about 1 wt % to about 7 wt %, or from about 1 wt % to about 5 wt %.

According to various embodiments, the hygiene product may be in the form of a substantially non-aqueous liquid or gel cleansing product, such as a shampoo, a conditioner, a bodywash, or any combination thereof, such as a combined shampoo, bodywash, and/or conditioner. In other embodiments, the hygiene product may be in the form of a substantially non-aqueous shaving product, such as a shaving gel, cream, liquid, or the like.

The hygiene product may include active agents dispersed in a multifunctional carrier. The active agent may include a surfactant and/or a surfactant system comprising a mixture of surfactants, one or more cleansing agents, and/or one or more conditioning agents. The conditioning agents may be configured to counteract the inherent harshness of the surfactants. The conditioning agents, carrier, thickeners (e.g., gellants), and/or secondary ingredients may be configured to increase the integrity of a pod and/or may operate to disperse the active agent when the pod is dissolved in water.

In various embodiments, the active agents may be in the form of a concentrate, such as shampoo concentrate, a conditioner concentrate, a bodywash concentrate, or any combinations thereof. The active agents may be in the form of a shaving product concentrate in other embodiments. In some embodiments, the active agent may include one or more of the above components in a powdered format.

The multifunctional carrier may be configured such that the hygiene product has rheological properties that are expected by consumers, may facilitate encapsulation of the hygiene product in a water-soluble envelope, and may operate to maintain the long-term stability of the hygiene product and/or the envelope.

In various embodiments, the carrier may operate as surfactant vehicle and/or solvent. In some embodiments, the carrier may be selected or configured to lower the overall reactivity of the hygiene product and the envelope. For example, the carrier may operate to control the free water percentage of the hygiene product.

In some embodiments, the carrier may be a non-aqueous liquid and/or may be configured to moisten pod components. In some embodiments, the carrier may also operate as a conditioner for hair and/or skin. The carrier may include, for example, polyols, polyglycerols, phospholipids, liquid amides, or combinations thereof.

Surfactants

In various embodiments, the active agents of the hygiene product may include one or more cleansing agents, such as surfactants. For example, the hygiene product may include anionic, nonionic, and/or amphoteric surfactants. In some embodiments, the hygiene product may include a surfactant system including a combination of different surfactants. The following surfactants may be referred to herein as "primary surfactants".

Non-limiting examples of suitable anionic surfactants include alkali metal sulforicinates, sulfonated glyceryl esters of fatty acids, such as sulfonated monoglycerides of coconut oil acids, salts of sulfonated monovalent alcohol esters such as sodium oleylisethianate, metal soaps of fatty acids, amides of amino sulfonic acids such as the sodium salt of oleyl methyl tauride, sulfonated products of fatty acids nitriles, such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanolamine lauryl sulfate, ether sulfates having alkyl groups of 8 or more carbon atoms, such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, calcium salts, decylbenzenesulfonic acid sodium salt, dodecylbenzenesulfonic acid sodium salt, cetylbenzenesulfonic acid sodium salt, and myristylbenzenesulfonic acid sodium salt, sulphuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnapthylsulfonic acid.

Non-limiting examples of suitable cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines, such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, trimethylammonium hydroxide, methylpolyoxyethylene cocoammonium chloride, and dipalmityl hydroxyethylammonium methosulfate, amide derivatives of amino alcohols such as beta-hydroxylethyl-stearylamide, and amine salts of long chain fatty acids.

Non-limiting examples of suitable cationic surfactants include also quaternary ammonium halides such as octyl trimethyl ammonium chloride, dodecyl trimethyl ammonium chloride, hexadecyl trimethyl ammonium chloride, octyl dimethyl benzyl ammonium chloride, decyl dimethyl benzyl ammonium chloride and coco trimethyl ammonium chloride as well as other salts of these materials, fatty amines and basic pyridinium compounds, quaternary ammonium bases of benzimidazolines, polypropanolpolyethanol amines, polyethoxylated quaternary ammonium salts and ethylene oxide condensation products of the primary fatty amines, available from Armak Company, Chicago, Ill. under the tradenames Ethoquad, Ethomeen, or Arquad. Suitable cationic surfactants can also be an esterquat-type compound.

In some embodiments, stearamidopropyl dimethylamine is a cationic, flaked, solid tertiary amine surfactant that may be included in the hygiene product. Stearamidopropyl dimethylamine is an effective conditioning agent and emulsifier. Stearamidopropyl dimethylamine also improves wet combing and feel, lowers dry hair friction, and softens hair.

Non-limiting examples of suitable nonionic surfactants include capryloyl/caproyl methyl glucamide and lauroyl/myristoyl methyl glucamide, lauryldimethylamine oxide (e.g., lauramine oxide), decyl glucosides, polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters. Suitable nonionic surfactants include condensates of ethylene oxide with a long chain (fatty) alcohol or (fatty) acid, condensates of ethylene oxide with an amine or an amide, condensation products of ethylene and propylene oxides, fatty acid alkylol amide and fatty amine oxides. Examples of non-ionic surfactants include polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol, and alkylpolysaccharides.

Non-limiting examples of suitable amphoteric surfactants include aliphatic secondary or tertiary amine derivatives in which the aliphatic radical is a linear or branched chain containing 8 to 22 carbon atoms and containing-at least one water-soluble anionic group (for example carboxylate, sulphonate, sulphate, phosphate or phosphonate); mention may also be made of $(C_8-C_{20})$alkyl-betaines, sulphobetaines, $(C_8-C_{20})$alkylamido$(C_1-C_6)$alkyl-betaines, or $(C_8-C_{20})$alkylamido$(C_1-C_6)$alkylsulphobetaines. In some embodiments, bocamidopropyl betaine (CAPB) may be included in the hygiene product as an amphoteric surfactant.

In some embodiments, environmentally friendly surfactants may be used, such as sulfate-free surfactants, such as sodium lauryl sulfoacetate, alpha olefin sulfonate, or the like, or combinations thereof.

In some embodiments, the hygiene product may include surfactants derived from natural oils, such as coconut oil, safflower oil, or the like, or natural materials such as sugar. For example, the hygiene product may include a sodium cocoyl isethionate (Hostapon SCI-85 C, manufactured by Clariant Corp.), cocamidopropyl betaine (Chembetaine C-42, manufactured by Lubrizol Corp.), cocamidopropyl hydroxysultaine (Chembetaine CAS manufactured by Lubrizol Corp.), capryloyl/caproyl methyl glucamide and lauroyl/myristoyl methyl glucamide (GlucoTain Plus, manufactured by Clariant Corp.), sodium methyl 2-sulfolaurate (Alpha Step PC-48, manufactured by Stepan Co.), alkyl polyglucoside (Pantaren 2000, manufactured by BASF Corp.) lauramine oxide (Mackamine LO, manufactured by Solvay Novecare Corp.), or combinations thereof.

In various embodiments, the hygiene product may include a mixture of primary surfactants, such as nonionic surfactants or a combination of nonionic and anionic surfactants. For example, the hygiene product may include the surfactant mixture in an amount ranging from about 5 wt % to about 50 wt %, such as from about 10 wt % to about 40 wt %, from about 20 wt % to about 35 wt %, from about 16 wt % to about 34 wt %, or from about 17 to about 33 wt %.

In some embodiments, such as in shampoo and/or bodywash applications, the surfactant system may be free of cationic surfactants. In other words, cationic surfactants may be excluded from the hygiene product in certain applications.

In some embodiments, the surfactant system may include at least one nonionic surfactant in an amount ranging from about 7 wt % to about 25 wt %, such as from about 8 wt % to about 22 wt %, or from about 9 wt % to about 20 wt %.

In some embodiments, the surfactant system may include at least one anionic surfactant in an amount ranging from about 0 wt % to about 25 wt %, such as from about 8 wt % to about 22 wt %, or from about 9 wt % to about 20 wt %.

In some embodiments, the surfactant system may have an anionic surfactant to nonionic surfactant weight ratio ranging from about 0 to about 2, such as from about 0.5 to about 1.9, or from about 1.3 to about 1.4.

In some embodiments, the surfactant system may include surfactants selected from sodium cocoyl isothionate, cocamidopropyl hydroxysultaine, capryloyl/caproyl methyl glucamide and lauroyl/myristoyl methyl glucamide, sodium methyl 2-sulfolaurate, alkyl polyglucoside, or any combinations thereof.

Polyols

In some embodiments, the carrier may include one or more polyols that are compatible with envelope materials such as PVOH. For example, the polyols may include nonvolatile, low molecular weight molecules that can modify the PVOH polymer matrix, thereby increasing free volume and chain mobility. Accordingly, one or more of the polyols may function as a plasticizer to improve the flexibility and processability of the envelope.

The polyols may also operate as solvents, humectants, and/or may control viscosity. In some embodiments, the hygiene product may include a mixture of two or more polyols. For example, the hygiene product may include from about 5 wt % to about 35 wt %, such as from about 10 wt % to about 30 wt %, from about 15 wt % to about 25 wt %, or about 20 wt %, of the polyol mixture.

In some embodiments, the polyols may include glycols and glycerin. For example, the glycols may be selected from ethylene glycol, poly(ethylene glycol), butylene glycol (e.g., 1,3-butylene glycol), hexylene glycol, or dipropylene glycol. In some embodiments, the polyol mixture may include of at least two glycols, at least three glycols, or at least four glycols, and may additionally include glycerin.

Hexylene glycol may provide anti-microbial activity, emolliency, moisturization, and/or skin conditioning effects to the hygiene product. Hexylene glycol may also operate to stiffen the envelope.

According to various embodiments, the hygiene product may include from 0 wt % to about 5 wt %, such as from about 0.5 wt % to about 4 wt %, or from about 1 wt % to about 3 wt % hexylene glycol. In some embodiments, the hexylene glycol content may be limited to about 2 wt %, in order to reduce eye irritation.

Propylene glycol is highly hydrophilic and may operate as a humectant that moisturizes the skin and/or hair. Propylene glycol may also operate as a solvent to the active agents and may operate as a plasticizer with respect to the envelope.

According to various embodiments, the hygiene product may include, based on the total weight of the hygiene product, from about 5 to about 25 wt %, such as from about 10 wt % to about 20 wt %, or about 15 wt % propylene glycol. In some embodiments, the polyol mixture may include propylene glycol primary component. In other words, the polyol mixture may include more propylene glycol than other polyols.

Glycerin operates as an active ingredient solvent, an envelope plasticizer, and a humectant. According to various embodiments, the hygiene product may include from about 0.5 wt % to about 15 wt %, such as from about 1 wt % to about 10 wt %, or from about 3 wt % to about 8 wt % glycerin. In some embodiments, the glycerin content may be limited to 8 wt % or less, to reduce and/or prevent degradation to the envelope.

Di-propylene glycol is a highly effective solvent, solubilizing agent, and carrying agent for fragrances. The hygiene product may include an amount of di-propylene glycol sufficient to solubilize an amount of fragrance oils and/or essential oils included in the hygiene product. For example, the hygiene product may include a 2:1 weight ratio of di-propylene glycol to fragrances and/or essential oils.

According to various embodiments, the hygiene product may include from 0 wt % to about 7 wt %, such as from about 0.1 wt % to about 6 wt %, or about 2 wt % to about 5 wt % di-propylene glycol.

Butylene glycol operates as a humectant that moisturizes the skin and/or hair. Butylene glycol may also operate as a solvent with respect to the active agents, and may operate as a plasticizer with respect to the envelope. Butylene glycol may also operate as a conditioning agent.

According to various embodiments, the hygiene product may include, based on the total weight of the hygiene product, from 0 wt % to about 10 wt %, such as from about 0.5 wt % to about 8 wt %, or from about 2 wt % to about 6 wt %, butylene glycol. In some embodiments, the butylene glycol content may be limited to 10 wt % or less, in order to prevent an excessive viscosity increase in the hygiene product. In some embodiments, the hygiene product may be free of butylene glycol.

Polyglyceryl Fatty Acid Esters

According to various embodiments of the present disclosure, the carrier may include one or more polyglyceryl fatty acid esters (PGEs) configured to provide emulsification and/or increase foaming. The PGEs may operate to solvate the active agents without reducing envelope stability.

The PGEs may include polyglyceryl monoesters and multi-esters. In shampoo and bodywash applications, the PGEs may have a hydrophilic-lipophilic balance (HLB) value of at least 9, such as at least 10 or at least 11. For example, the PGEs may include polyglyceryl-2 caprate, polyglyceryl-3 caprate, polyglyceryl-3 laurate, polyglyceryl-6 esters, or any combinations thereof.

In various embodiments, the hygiene product may include from about 0.1 to about 60 wt %, such as from about 10 wt % to about 50 wt %, from about 12 wt % to about 45 wt %, or from about 15 wt % to about 35 wt % of one or more PGEs.

Polyglyceryl-2 caprate is a liquid compound derived from polyglycerin and a fatty acid. Polyglyceryl-2 caprate may operate as an emulsifier to create fine, creamy bubbles, especially when combined with anionic surfactants. It is an excellent thickener with good thermostable viscosity. Polyglyceryl-2 caprate can be used as deodorizing ingredient because of its reaction to gram-positive bacteria making it an ideal addition for anhydrous body wash and shampoo formulations.

The hygiene product may include, from about 0 wt % to about 50 wt %, such as from about 0.1 wt % to about 40 wt %, or from about 5 wt % to about 30 wt %, polyglyceryl-2 caprate. Amounts of over 50 wt % are possible, but prevent the hygiene product from including appropriate amounts of other ingredients, such as surfactants, conditioning agents, etc., for a given application.

Polyglyceryl-3 caprate is a liquid nonionic co-surfactant and refatting agent with an estimated HLB value of 10-13. This PEG-free refatting agent helps to prevent the skin from drying and provides a luxurious and soft skin feel. It also provides a mild antimicrobial and deodorizing effect.

The hygiene product may include from about 0 wt % to about 25 wt %, such as from about 0.1 wt % to about 20 wt %, or from about 5 wt % to about 15 wt %, polyglyceryl-3 caprate. It is believed that polyglyceryl-3 caprate amounts of greater than 25% may result in decreased foam height and bubble size in some formulations.

In some embodiments, the hygiene product may include polyglyceryl-2 caparate esters in an amount ranging from about 10 wt % to about 30 wt %, and polyglyceryl-3 caparate in an amount ranging from about 4 wt % to about 24 wt %.

Polyglyceryl-3 laurate may provide moisturization, humectant, and emollient properties in both hair and skin formulations. Polyglyceryl-3 laurate is also completely dispersible in water.

The hygiene produce may include from about 0 wt % to about 30 wt %, such as from about 0.1 wt % to about 20 wt %, or from about 5 wt % to about 18 wt %, polyglyceryl-3 laurate. It is believed that polyglyceryl-3 laurate amounts of greater than 20 wt % may result in decreased foam height and bubble size in some formulations.

Sunflower oil polyglyceryl-6 esters may be obtained by the transesterification of sunflower seed oil and polyglycerin-6. The compound is an amphiphilic ester that promotes shine and skin and hair softening attributes without negatively affecting the foam by contributing to emollient overload.

The hygiene product may include from about 0 to about 15 wt %, such as from about 0.1 wt % to about 12 wt %, from about 1 wt % to about 11 wt %, or from about 2 wt % to about 7 wt %, polyglyceryl-6 esters. It is believed that the hygiene product may include polyglyceryl-6 esters in amounts of up to 50 wt %. However, amounts of 15 wt % or less may be preferable due to the extreme cost and low commercial availability of this ingredient.

In some embodiments, the hygiene product may include polyglyceryl-6 esters in an amount ranging from about 1 wt % to about 11 wt %, and polyglyceryl-2 caparate in an amount ranging from about 5 wt % to about 15 wt %.

In conditioning applications, the hygiene product may include PGEs having HLB values of about 9 or less, such as about 8 or less, or about 6 or less. In such hygiene products, the PGEs may be used in conjunction with cationic conditioning agents and triglycerides.

Liquid Amides

According to various embodiments of the present disclosure, the hygiene product may include one or more liquid amides. The liquid amides may be configured to operate as secondary surfactants, solubilizers, emollients, and/or emulsifiers.

For example, the hygiene product may include one or more liquid amides in an amount ranging from about 0 wt % to about 45 wt %, such as from about 5 wt % to about 40 wt %, from about 6 wt % to about 20 wt %, or from about 8 wt % to about 15 wt %.

For example, lactamide monoethanolamine (LMEA) (Pheonamid LMEA, available from Phoenix Chemical, Inc.) is a liquid amide humectant that may impart smooth, nongreasy feel and sheen to skin and/or hair.

In various embodiments, the hygiene product may include LMEA in an amount ranging from about 0 wt % to about 20 wt %, such as from about 1 wt % to about 15 wt %, from about 2 wt % to about 12 wt %, or from about 3 wt % to about 9 wt %.

Dimethyl lauramide/myristamide (Ninol CAA, available from Stephan Co.) is a liquid amide secondary surfactant configured to optimize carrier characteristics without reducing cleansing performance. Ninol CAA is a nitrosamine-free, 100% active, liquid amide that enables the imperceptible reduction of surfactant levels, solubilizes fragrances, and may substitute other amides.

In various embodiments, the hygiene product may include Ninol CAA in an amount ranging from about 0 wt % to about 20 wt %, such as from about 1 wt % to about 15 wt %, from about 3 wt % to about 10 wt %, or from about 2 wt % to about 4 wt %.

Lauryl lactyl lactate (Stepan-Mild L3, available from Stephan Co.) is a naturally-derived, multi-functional emollient/surfactant liquid amide formed as the product of reacting lauryl alcohol and lactic acid. Stepan-Mild L3 may operate as a viscosity builder, foam booster, emulsifier, and emollient.

In various embodiments, the hygiene product may include STEPAN-MILD L3 in an amount ranging from about 0 wt % to about 20 wt %, such as from about 0.5 wt % to about 15 wt %, from about 1 wt % to about 10 wt %, or from about 2 wt % to about 7 wt %.

Phospholipids

According to various embodiments of the present disclosure, the hygiene product may include one or more phospholipids configured to operate as a foam enchancer and/or cleanser. For example, the hygiene product may include from about 0 wt % to about 20 wt %, such as from about 1 wt % to about 15 wt %, or from about 5 wt % to about 10 wt % of one or more phospholipids.

In some embodiments, the hygiene product may include phospholipids selected from cocamidopropyl PG-dimonium chloride phosphate (Cola Lipid C, manufactured by Colonial Chemical Inc.), linoleamidopropyl PG-dimonium chloride phosphate (Cola Lipid SAFL, manufactured by Colonial Chemical Inc.), or combinations thereof.

In some embodiments, the hygiene product may include substantially equal amounts of different phospholipids. For example, the hygiene product may include substantially equal amounts of Cola Lipid C and Cola Lipid SAFL.

Additional Conditioners

In some embodiments, the hygiene product may include one or more additional conditioners. Non-limiting examples of suitable additional conditioners include petrolatum, fatty acids, esters of fatty acids, fatty alcohols, ethoxylated alcohols, polyol polyesters, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters, triglycerides and mixtures thereof.

Preferable additional conditioners may include pyrrolidone carboxylic acid (PCA) glyceryl Oleate (SOFTISAN conditionHAIR, available from IOI Oleo GmbH), which is a natural skin and hair conditioning agent, and betaine (Genencare OSMS BA, available from DuPont Nutrition and Biosciences Inc.).

Additional Emulsifiers/Stabilizers

In various embodiments, the hygiene product may include one or more additional emulsifiers that may operate to further stabilize the hygiene product. For example, the hygiene product may include non-ionic, oil-in-water emulsifiers configured to create a lamellar or bilayered structure. For example, the emulsifiers may include non-ionic emulsifiers, such as, a mixture of cetearyl alcohol and cetearyl glucoside (Monatov 68, available from Seppic Corp.), glycerol stearate (Lipo GMS 450, available from Lipo Chemicals Corp.), or a combination thereof.

In some embodiments, the hygiene product may include a non-ionic, oil-in-water emulsifier in an amount ranging from about 0 wt % to about 3 wt %, such as from about 0.2 wt % to about 2 wt %, or from about 0.8 wt % to about 1.3 wt %.

In some embodiments, the emulsifiers may include hygroscopic polymers, such as guar gum (e.g., *Cyamopsis tetragonoloba* gum), cationic guar gum, xanthan gum, starch, pregelatinized starch, modified starches, such as hydroxypropyl starch phosphate and sodium starch glycolate, honey, polyvinyl pyrolidone (PVP), ExpertGel EG312 (poloxamer 338/PPG-12/SMDI copolymer) available from DKSH Inc., ExpertGel EG412 (poloxamer 407, PPG-12/SMDI copolymer) available from DKSH Inc, combinations thereof, or the like. In some embodiments, the thickeners may include cellulose derivatives such as carboxymethyl cellulose, cellulose gum, or tylose powder. In some embodiments, the hygiene product may include a polyoxyethylene ether.

In some embodiments, the emulsifiers may include a hydroscopic polymer thickener in an amount ranging from about 0 wt % to about 0.4 wt %, such as from about 0.05 wt % to about 0.3 wt %, or from about 0.1 wt % to about 0.2 wt %.

For example, the hygiene product may include a modified starch thickener in an amount ranging from about 0.1 wt % to about 3 wt %, such as from about 0.2 wt % to about 2 wt %, or from about 0.3 wt % to about 1 wt %.

In some embodiments, the thickeners may include non-ionic surfactants configured to form a lamellar network. For example, the thickeners may include a lamellar network formed from polyoxyethylene ethers including a mixture of high molecular mass saturated fatty alcohols, mainly cetyl alcohol and stearyl alcohol, such as ceteareth-20. In some embodiments, the hygiene product may include a nonionic surfactant in an amount ranging from about 8 wt % to about 18 wt %, such as about 12 wt %.

Carrier Diffusion Control

In some embodiments, the envelope of the hygiene product pod may have some amount of permeability with respect to the hygiene product. This could lead to diffusion of one or more components of the hygiene product through the envelope over time, which may reduce pod shelf-life. For example, an envelope formed of PVOH could inherently have some amount permeability with respect the butylene glycol carrier. Accordingly, the hygiene product may include thickeners configured to reduce carrier permeation through the envelope.

In various embodiments, thickeners such as carboxymethyl cellulose, cellulose gum, or tylose powder may be optionally added to the hygiene product to reduce diffusion through the envelope. For example, tylose powder may be added to the hygiene product in an amount ranging from about 0.05 wt % to about 0.5 wt %, such as from about 0.15 wt % to about 0.25 wt %, or about based on the total weight of the hygiene product.

Secondary Ingredients

In various embodiments, the hygiene product pods may include secondary ingredients. For example, the secondary ingredients may include buffers/pH adjusters, dyes/colorants, moisturizers, fragrances, vitamins, texture modifiers, essential oils, foam enhancers, and anti-microbial agents, combinations thereof, or the like. In various embodiments, hygiene products may include from about 0 wt % to about 8 wt % secondary ingredients.

The buffers/pH adjusters may include calcium ions, potassium ions, or hydroxide ions, any combination thereof, or any salts or compounds capable of generation such ions. The buffers/pH adjusters may be blended at various ratios, in order to provide a suitable pH. For example, a suitable amount of buffer/pH adjuster may be added to the hygiene product to provide a slightly acidic pH for compatibility with PVOH envelopes. For example, the hygiene product may advantageously have a room temperature pH ranging from about 5 to about 9, such as from about 4.8 to about 6.9, or from about 5.0 to about 6.8.

In some embodiments, the secondary ingredients may include essential oils such as argan oil, sunflower oil, lavender oil, rosemary oil, cedar wood oil, thyme oil, peppermint oil, chamomile oil, sage oil, lemon oil, patchouli oil, tea tree oil, ylang oil, vetiver oil, carrot seed oil, cypress oil, helichrysum oil, combinations thereof, or the like.

In some embodiments, hygiene products may include moisturizers such as betaine (Genencare OSMS BA, manufactured by Dupont Corp.). In some embodiments, hygiene products may include vitamins such as tocopherol, DL Panthenol, or combinations thereof.

Secondary ingredients useful for improving dissolvability and/or foaming may include coconut milk powder, arrow root powder, colloidal oatmeal powder, combinations thereof, or the like. In various embodiments, hygiene products may include a secondary ingredient, such as coconut milk powder, arrow root powder, colloidal oatmeal powder, or any combination thereof, in an amount ranging from about 0 wt % to about 22 wt %, such as from about 5 wt % to about 20 wt %, or from about 8 wt % to about 15 wt %. Colloidal oatmeal powder may also operate as a texture modifier to provide a smoother texture.

Any suitable colorant may be used. Hygiene products may include a colorant in an amount ranging from about 0 wt % to about 0.3 wt %, such as from about 0.1 wt % to about 0.2 wt %.

In various embodiments, a suitable fragrance may be used. Useful fragrances may be in liquid form, such as traditional fragrances that are combinations of synthetic and natural compounds, natural fragrances that consist of a blend of natural extracts and essential oils, or essential oils in the pure and neat form. Hygiene products may include a fragrance oil in an amount ranging from about 0 wt % to about 0.3 wt %, such as from about 0.1 wt % to about 0.2 wt %.

In various embodiments, texture modifiers may include micro or macro abrasive agents, such as when a pod includes a body scrub. Suitable abrasive agents include, for example, nut powders, silica powders, polymer beads such as wax beads, combinations thereof, or the like. In some embodiments, hygiene products may include an abrasive agent in an amount ranging from about 0 wt % to about 3 wt %, such as from about 0.1 wt % to about 2 wt %, or from about 0.2 wt % to about 1 wt %.

In various embodiments, anti-microbial agents may be natural materials having anti-microbial effects. For example, anti-microbial agents may include thyme oil, tea tree oil, oregano oil, lavender oil, citrus essential oil, grapefruit seed extract, olive leaf extract, honey, or the like. Hygiene products may include an anti-microbial agent in an amount ranging from about 0 wt % to about 3 wt %, such as from about 0.1 wt % to about 2 wt %, or from about 0.2 wt % to about 1 wt %.

Method of Using Hygiene Product Pods

Figure 4:
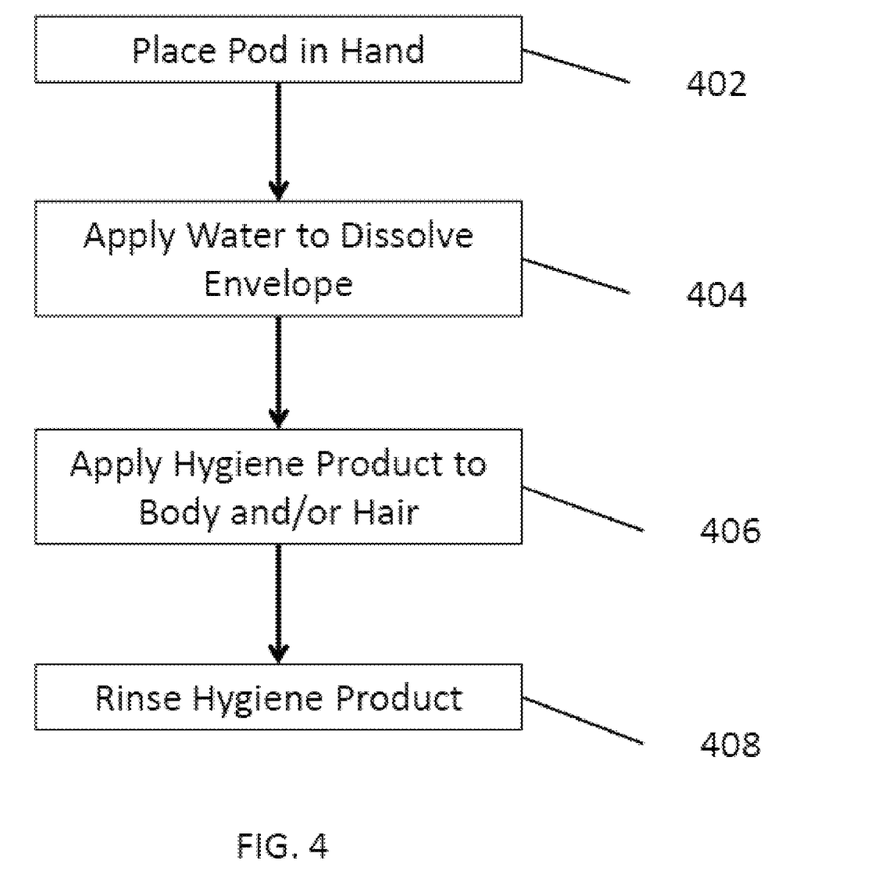
FIG. 4 is a block diagram illustrating a method of using a hygiene product pods, according to various embodiments of the present disclosure.

FIG. 4 is a process flow diagram illustrating a method of using a hygiene product pod according to various embodiments. Referring to FIG. 4, in step 402, a pod as described above may be removed from a container or packaging and may be placed in the hand of a user. The container may include multiple pods and may be configured to limit the exposure of the pods contained therein to moisture. For example, the container may be formed of water resistant paper or paperboard, such as the types of paper used for packaging soap, sugar, or flour. In other embodiments, the pods may be packaged in biodegradable or recyclable packs, for example, in blister packs, polylactic acid bags, for example. Accordingly, the pods may be packaged in a single dose format with minimal environmental impact.

In step 404, water is applied to the pod, such as while holding the pod in one's hands. In some embodiments, friction and/or agitation may also optionally be applied to the pod. The pod may remain in contact with the water in the user's hand and the optional friction may be applied, for a time period sufficient for the water to dissolve the envelope of the pod and release the hygiene product contained therein. For example, a time period for completely or substantially completely dissolving the envelope of the pod may range from about 0.5 seconds to about 1 minute, such as from about 1 second to about 30 seconds, from about 1 second to about 20 seconds, or from about 1 second to about 10 seconds. The dissolution time may vary according to an amount of applied friction and/or the temperature of the applied water (e.g., increased friction and/or water temperatures may result in a reduced dissolution time).

In step 406, the hygiene product is applied to the body of the user. For example, the hygiene product may be applied to the hair of the user, when the hygiene product is in the form of a shampoo and/or a combined shampoo, conditioner, and/or bodywash. In other embodiments, hygiene product may be applied to the body and/or hair of the user, when the hygiene product is in the form of bodywash, a combined shampoo and bodywash, and/or a combined bodywash, shampoo, and conditioner. In other embodiments, the hygiene product may be applied to areas of the user's skin where hair is intended to be removed, when the hygiene produce is in the form of a shaving product.

In step 408, the hygiene product may be rinsed from the applied area or areas.

Exemplary Formulations

The following Tables 1 and 2 include Examples 1-15 of exemplary hygiene product compositions according to various embodiments of the present disclosure. The following Table 3 includes Comparative Examples 1-5 of comparative hygiene product compositions.

TABLE 1

| Component | Ex. 1 Wt. % | Ex. 2 Wt. % | Ex. 3 Wt. % | Ex. 4 Wt. % | Ex. 5 Wt. % | Ex. 6 Wt. % | Ex. 7 Wt. % |
| --- | --- | --- | --- | --- | --- | --- | --- |
| Hostapon SCI-85 P | 13 | 14.3 | | 11 | | 8 | 10.5 |
| Chembetaine CAS | 3 | 3 | 3 | 3 | 3 | 3 | 3 |
| Glucotain Plus | 6 | 9 | 6 | 6 | 6 | 5 | 8.5 |
| Alpha Step PC-48 | | | | | | | 6 |
| Alkyl Polyglucoside | | | 8 | 11 | 11 | 2 | 1 |
| Propylene Glycol | 5 | 9 | 9 | 9 | 11 | 11.5 | 14 |
| Hexylene Glycol | 2 | 2 | 2 | 2 | 2 | 2 | 2 |
| Di-propylene Glycol | 7 | 6 | 6 | 5 | 6 | 4 | 2 |
| Glycerin | 3 | 4 | 4 | 4 | 4 | 4 | 6 |
| Polyglyceryl-6 Est. | | | | 10 | 10 | 7 | 3 |
| Polyglyceryl-3 Cap. | | | | | | | |
| Polyglyceryl-2 Cap. | | | 12.5 | 10.5 | 10.9 | 10 | 14 |
| Cola Lipid C | 5 | 4 | 4 | 4 | 4 | 4 | 4 |
| Cola Lipid SAFL | 3 | 2 | 2 | 2 | 2 | 2 | 2 |
| Phoenamid LMEA | 11 | 11 | 11 | 8 | 9 | 9.1 | 7.8 |
| Stepan Mild L3 | 10.85 | 12 | 13 | 2 | 4 | 4 | 5 |
| Nino CAA | 10.85 | 11 | 12 | 2 | 4 | 4 | 3 |
| Additives | 19.2 | 9.4 | 7.5 | 10 | 13.1 | 11.4 | 6.6 |

TABLE 2

| Component | Ex. 8 Wt. % | Ex. 9 Wt. % | Ex. 10 Wt. % | Ex. 11 Wt. % | Ex. 12 Wt. % | Ex. 13 Wt. % | Ex. 14 Wt. % | Ex. 15 Wt. % |
| --- | --- | --- | --- | --- | --- | --- | --- | --- |
| Hostapon SCI-85 P | 11.5 | 9 | 13 | 8 | 11 | 13 | 10 | 11.5 |
| Chembetaine CAS | 3 | 3 | 3 | 3 | 3 | 3 | 3 | 3 |

TABLE 2-continued

| Component | Ex. 8 Wt. % | Ex. 9 Wt. % | Ex. 10 Wt. % | Ex. 11 Wt. % | Ex. 12 Wt. % | Ex. 13 Wt. % | Ex. 14 Wt. % | Ex. 15 Wt. % |
|---|---|---|---|---|---|---|---|---|
| Glucotain Plus | 8.5 | 5.5 | 5.5 | 5.5 | 5.5 | 5.5 | 5.5 | 5.5 |
| Alpha Step PC-48 | 6 | 3.5 | 4.5 | 4.5 | 5.5 | 5.5 | 5 | 4.35 |
| Alkyl Polyglucoside | 1 | 1 | 1 | 1 | 1 | 1 | 1.2 | 1.5 |
| Propylene Glycol | 18.5 | 14 | 14 | 5 | 15 | 15 | 14 | 14 |
| Hexylene Glycol | 2 | 2 | 2 | 2 | 2 | 2 | 2 | 2 |
| Di-propylene Glycol | | | | | | | | |
| Glycerin | 6 | 4.1 | 4.1 | 4.1 | 4.1 | 4.1 | 4.1 | 4.1 |
| Polyglyceryl-6 Est. | 2.6 | | | | | | | |
| Polyglyceryl-3 Cap. | | 20 | 15 | 23 | 8 | 8 | 7.95 | 7.95 |
| Polyglyceryl-2 Cap. | 18.5 | 13 | 13 | 24 | 21 | 21.5 | 25 | 26 |
| Cola Lipid C | 4 | 4 | 4 | 4 | 4 | 4 | 4.5 | 4.5 |
| Cola Lipid SAFL | 2 | 2 | 2 | 2 | 2 | 2 | 2 | 2 |
| Phoenamid LMEA | 3 | 3 | 3 | 3 | 3 | 3 | 3 | 3 |
| Stepan Mild L3 | 5 | 7 | 7 | 2 | 7 | 5 | 7 | 7 |
| Nino CAA | 3 | 3 | 3 | 3 | 3 | 3 | 2 | 0 |
| Additives | 4.6 | 4.6 | 4.6 | 4.6 | 3.6 | 4.4 | 3.7 | 3.6 |

TABLE 3

| Component | Comp. Ex. 1 Wt. % | Comp. Ex. 2 Wt. % | Comp. Ex. 3 Wt. % | Comp. Ex. 4 Wt. % | Comp. Ex. 5 Wt. % |
|---|---|---|---|---|---|
| Hostapon SCI-85 P | 13 | 13 | 13 | 13 | 13 |
| Chembetaine CAS | 5.8 | 5 | 9.6 | 5 | 6 |
| Glucotain Plus | 11 | 11 | 10 | 11 | 11 |
| Alpha Step PC-48 | | | | | |
| Alkyl Polyglucoside | | | | | |
| Butylene Glycol | 25 | 10 | 25 | 0 | 25 |
| Propylene Glycol | 0 | 9 | 2.4 | 18 | 0 |
| Hexylene Glycol | 2 | 2 | 2 | 2 | 2 |
| Di-propylene Glycol | | | | | |
| Glycerin | | | | | |
| Polyglyceryl-6 Est. | | | | | |
| Polyglyceryl-3 Cap. | | | | | |
| Polyglyceryl-2 Cap. | | | | | |
| Cola Lipid C | 5 | 7 | 0 | 6.5 | 5 |
| Cola Lipid SAFL | 5 | 7 | 0 | 6.5 | 3.2 |
| Phoenamid LMEA | 11 | 11 | 11 | 11 | 11 |
| Stepan Mild L3 | | | | | |
| Nino CAA | | | | | |
| Additives | 19.1 | 21.5 | 23.5 | 23.5 | 20.5 |

The components of each of Examples 1-12 and Comparative Examples 1-5 were mixed to form hygiene products. The hygiene products were then packaged to form pods using methods as described above. In particular, the hygiene products were encapsulated between sheets of PVOH using a roll coater and sealing device.

Figure 5A:
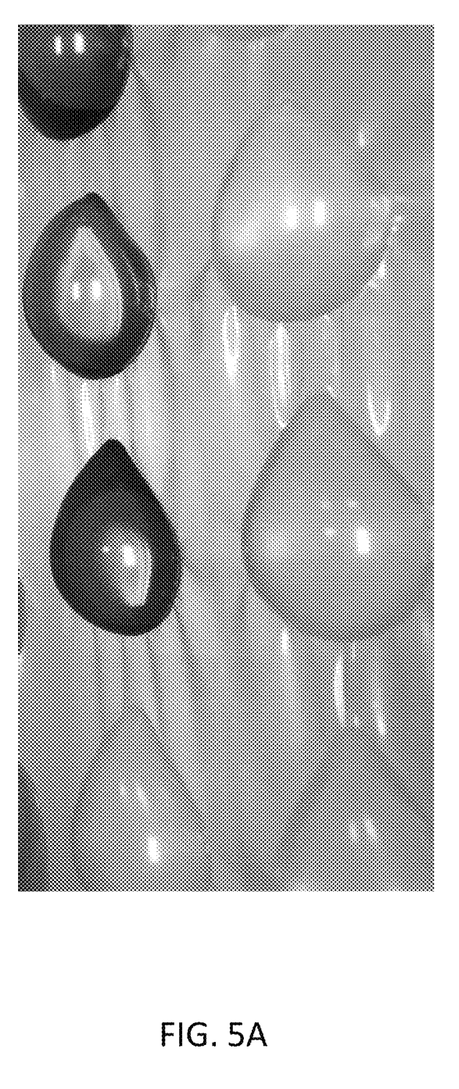
FIGS. 5A and 5B are photographs respectively showing hygiene product pods according to various embodiments of the present disclosure and comparative hygiene product pods.
Figure 5B:
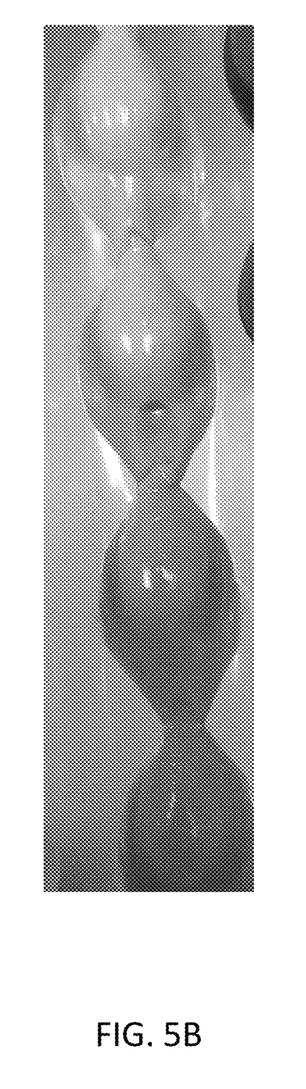

FIG. 5A a photograph showing a sheet formed by depositing and sealing of a composition according to one of Comparative Example 1, between two sheets of PVOH, and FIG. 5B is a photograph showing a sheet formed by the deposition and sealing of the hygiene product according to one of Example 1, between two sheets of PVOH.

As shown in FIG. 5A, the comparative hygiene product had a relatively high viscosity, which resulted in tailing between deposits of the comparative hygiene product. In particular, the viscosity of the comparative hygiene product caused the product to form a "tail" between the deposits of the product on the underlying PVOH sheet and the deposition apparatus. As a result, the deposits overlapped one another, and the sealing process did not produce discretely sealed deposits that could be cut into individual sealed pods. Similar results were obtained for Comparative Examples 2-5.

In particular, Comparative Examples 2-5 were formulated in an attempt to reduce the viscosity of the compositions and prevent tailing, by modifying the polyol amounts and compositions. Comparative Example 5 had the lowest viscosity. However, the sodium cocoyl isethionate was held in a gel like suspension that was still too viscus to prevent tailing or provide self-leveling in Comparative Example 5.

In contrast, as shown in FIG. 5B, the hygiene product of Example 1 had a relatively low viscosity that allowed for the formation of discrete deposits of the hygiene product on the underlying PVOH sheet. As such, the deposits could be discretely sealed and the sheet could be easily cut to form individual pods. Similar results were obtained for Examples 2-12.

In Examples 1-3 were compositions that included relatively high amounts of two the liquid amides, dimethyl lauramide/myristamide (Ninol CAA) and lauryl lactyl lactate (Stephan Mild L3). The addition of these liquid amides, combined with the removal of gelling agents, lowered the viscosity of the formulation. In particular, there was a gradual and slight improvement with regards to viscosity and thinning consistency as the total amounts of Ninol CAA and Stepan Mild 3 were increased from 22.7 wt % to 26 wt %. Unfortunately, there was a corresponding drop in foaming action and cleansing with the increase in liquid amides.

Example 3 included a polyglyceryl fatty acid ester (polyglyceryl-2 caprate) and a corresponding reduction in surfactant content. As a result, Example 3 exhibited a substantial reduction in foaming as compared to Examples 1 and 2.

Examples 4-8 were compositions that included a combination of two polyglyceryl fatty acid esters (polyglyceryl-2 caprate and polyglycerol-6 esters) and reduced amounts of liquid amides. In particular, higher amounts of polyglyceryl-2 caprate were found to reduce viscosity of the compositions without significantly reducing foaming and cleansing performance. As such, polyglyceryl-2 caprate was shown to provide functions similar to water used in conventional shampoo. The addition of polyglyceryl-2 caprate was also found to allow the drastic reduction in the amounts of Ninol CAA and Stepan Mild L3, which were thought to be limiting with respect to foam height and cleansing ability.

Examples 9-15 were composition that included combinations of polyglyceryl-2 caprate and polyglyceryl-3 caprate, with the polyglyceryl-3 caprate being used in place of the polyglyceryl-6 esters of Examples 4-8. In particular, Examples 9-15 included varying amounts of both SCI powder and polyglyceryl-3 caprate, in order to maximize foam height while maintaining a thin viscosity that is rapidly self-leveling. Examples 9-15 demonstrate that amounts of SCI powder ranging from about 9.5 wt % to about 10.5 wt % provide unexpectedly good foaming and viscosity characteristics. In addition, polyglyceryl-3 caprate amounts above about 8 wt % decrease foam bubble size and wall stability, which unexpectedly provides a rich milky lather that dissipates quickly and does not build.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. Thus, the present invention is not intended to be limited to the aspects and/or embodiments shown herein but is to be accorded the widest scope consistent with the following claims and the principles and novel features disclosed herein.

What is claimed is:

1. A hygiene product pod comprising:
   a water-soluble envelope; and an emulsified liquid hygiene product sealed in the envelope, the hygiene product comprising, based on the total weight of the hygiene product:
   surfactants in an amount ranging from about 10 wt % to about 40 wt %;
   a first polyol in an amount ranging from about 10 wt % to about 30 wt %;
   wherein the first polyol comprises, based on the total weight of the hygiene product:
   propylene glycol in an amount ranging from about 10 wt % to about 20 wt %;
   glycerin in an amount ranging from about 1 wt % to about 10 wt %;
   optionally di-propylene glycol in an amount less than 6 wt %; and
   hexylene glycol in an amount less than 5 wt %;
   a second polyol in an amount ranging from about 10 wt % to about 50 wt %, wherein the second polyol is at least one polyglyceryl fatty acid ester (PGE) selected from the group consisting of polyglyceryl-2 caprate, polyglyceryl-3 caprate, polyglyceryl-3 laurate, and polyglyceryl-6 esters; and
   liquid amides in an amount ranging from about 5 wt % to about 40 wt %,
   wherein the hygiene product has a free water content of about 9 wt % or less.

2. The hygiene product pod of claim 1, wherein the hygiene product comprises, based on the total weight of the hygiene product, the surfactants in an amount ranging from about 20 wt % to about 35 wt %.

3. The hygiene product pod of claim 2, wherein the surfactants are selected from non-ionic surfactants, anionic surfactants, or a combination thereof.

4. The hygiene product pod of claim 1, wherein the hygiene product comprises, based on the total weight of the hygiene product, the first polyol in an amount ranging from about 15 wt % to about 25 wt %.

5. The hygiene product pod of claim 1, wherein the first polyol comprises, based on the total weight of the hygiene product:
   the di-propylene glycol in an amount ranging from about 2 wt % to about 6 wt %; and
   the hexylene glycol in an amount ranging from about 1 wt % to about 3 wt %.

6. The hygiene product pod of claim 1, wherein the hygiene product comprises, based on the total weight of the hygiene product, the PGE in an amount ranging from about 12 wt % to about 45 wt %.

7. The hygiene product pod of claim 1, wherein the PGE has a hydrophilic-lipophilic balance (HLB) value of at least 9.

8. The hygiene product pod of claim 1, wherein the PGE comprises, based on the total weight of the hygiene product:
   polyglyceryl-6 esters in an amount ranging from about 1 wt % to about 11 wt %; and
   polyglyceryl-2 caprate in an amount ranging from about 5 wt % to about 15 wt %.

9. The hygiene product pod of claim 1, wherein the PGE comprises, based on the total weight of the hygiene product:
   polyglyceryl-2 caprate in an amount ranging from about 10 wt % to about 30 wt %; and
   polyglyceryl-3 caprate in an amount ranging from about 4 wt % to about 24 wt %.

10. The hygiene product pod of claim 1, wherein the hygiene product comprises, based on the total weight of the hygiene product, the liquid amides in an amount ranging from about 6 wt % to about 20 wt %.

11. The hygiene product pod of claim 1, wherein the liquid amides comprise, based on the total weight of the hygiene product:
    lactamide monoethanolamine (LMEA) in an amount ranging from about 1 wt % to about 15 wt %;
    lauryl lactyl lactate in an amount ranging from about 1 wt % to about 15 wt %; and
    dimethyl lauramide/myristamide in an amount ranging from about 1 wt % to about 15 wt %.

12. The hygiene product pod of claim 1, further comprising phospholipids in an amount up to about 20 wt %.

13. The hygiene product pod of claim 11, wherein the hygiene product comprises, based on the total weight of the hygiene product, the phospholipids in an amount ranging from about 1 wt % to about 15 wt %.

14. The hygiene product pod of claim 13, wherein the phospholipids comprise cocamidopropyl PG-dimonium chloride phosphate and linoleamidopropyl PG-dimonium chloride phosphate.

15. The hygiene product pod of claim 13, wherein the envelope comprises polyvinyl alcohol.

16. The hygiene product pod of claim 10, wherein the envelope comprises a polyvinyl alcohol (PVOH) film or a woven or non-woven polyvinyl alcohol (PVOH) fiber.

17. The hygiene product pod of claim 1, wherein the envelope has a thickness ranging from about 0.5 mm to about 5.0 mm.

18. The hygiene product pod of claim 1, wherein the hygiene product has a free water content of about 5 wt % or less, based on the total weight of the hygiene product.

19. A method of using the hygiene product pod of claim 1, comprising:
    applying water to the pod to dissolve the envelope and release the hygiene product;
    applying the hygiene product to at least one body part of a user; and
    rinsing the hygiene product from the body part.

20. The method of claim 19, wherein applying water comprises applying the water for a time period ranging from about 20 seconds to about 40 seconds to dissolve the envelope.

21. The hygiene product pod of claim 1, wherein the surfactants are selected from amphoteric surfactants, cationic surfactants, or a combination thereof.

* * * * *